(12) United States Patent
Traficante

(10) Patent No.: US 9,055,889 B2
(45) Date of Patent: Jun. 16, 2015

(54) METHOD AND APPARATUS FOR BREATH TESTING

(75) Inventor: Louis J. Traficante, Shohola, PA (US)

(73) Assignee: Commonwealth Laboratories, Inc., Salem, MA (US)

( * ) Notice: Subject to any disclaimer, the term of this patent is extended or adjusted under 35 U.S.C. 154(b) by 598 days.

(21) Appl. No.: 13/424,715

(22) Filed: Mar. 20, 2012

(65) Prior Publication Data
US 2013/0253361 A1   Sep. 26, 2013

(51) Int. Cl.
A61B 5/08 (2006.01)
A61B 5/097 (2006.01)

(52) U.S. Cl.
CPC ...................................... A61B 5/097 (2013.01)

(58) Field of Classification Search
CPC ....................................................... A61B 5/097
USPC ........................................................... 600/543
See application file for complete search history.

(56) References Cited

U.S. PATENT DOCUMENTS

| | | |
|---|---|---|
| 3,544,273 A | 12/1970 | McConnaughey |
| 3,817,108 A | 6/1974 | Principe |
| 3,853,477 A * | 12/1974 | Block et al. ...................... 422/85 |
| 4,158,360 A * | 6/1979 | Adams ........................... 600/538 |
| 4,671,298 A | 6/1987 | Babb |
| 4,852,583 A | 8/1989 | Walker |
| 4,951,512 A | 8/1990 | Mazza |
| 5,042,500 A | 8/1991 | Norlien |
| 5,042,501 A | 8/1991 | Kenny |
| 5,140,993 A | 8/1992 | Opekun |
| 5,467,776 A | 11/1995 | Hamilton |
| 6,326,364 B1 | 12/2001 | Lin |
| 6,468,477 B1 | 10/2002 | Hamilton |
| 6,562,629 B1 | 5/2003 | Lin |
| 6,565,814 B1 | 5/2003 | Anraku |
| 6,723,056 B1 * | 4/2004 | Alving et al. ................. 600/543 |
| 6,805,852 B2 | 10/2004 | Lin |
| 6,861,053 B1 | 3/2005 | Lin |
| 7,048,906 B2 | 5/2006 | Lin |
| 7,056,686 B2 | 6/2006 | Lin |
| 7,452,857 B2 | 11/2008 | Lin |
| 7,585,838 B2 | 9/2009 | Lin |
| 7,605,240 B2 | 10/2009 | Lin |
| 7,718,608 B2 | 5/2010 | Lin |
| 7,736,622 B2 | 6/2010 | Lin |
| 7,935,799 B2 | 5/2011 | Lin |
| 2005/0177057 A1 * | 8/2005 | Friedman et al. ............. 600/543 |
| 2010/0209507 A1 | 8/2010 | Lin |

* cited by examiner

Primary Examiner — Michael Kahelin
Assistant Examiner — Mitchell E Alter

(57) ABSTRACT

A breath sampling device includes a main housing having an input chamber, a first output chamber, and a second output chamber integrally formed therein where the input chamber and the first output chamber are coupled via a first port and the input chamber and the second output chamber are coupled via a second port, and a self-sealing apparatus within the second output chamber configured to seal at least an exhaust port of the second output chamber when a predetermined amount of initial waste air fills the second output chamber. The main housing can be configured to redirect a portion of air blown therethrough towards the output chamber via the first port when the self-sealing apparatus at least seals the exhaust port. Other embodiments are disclosed.

18 Claims, 7 Drawing Sheets

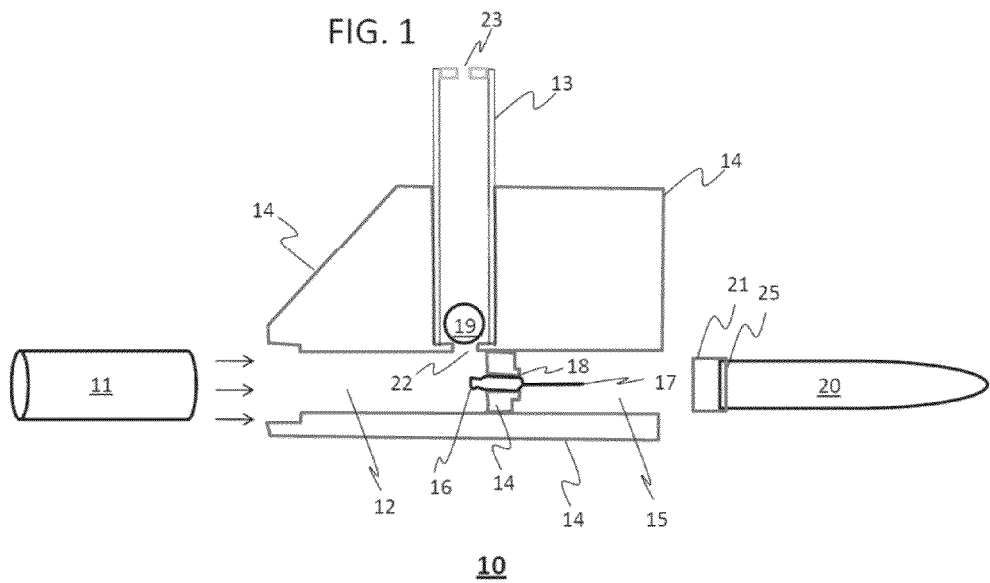
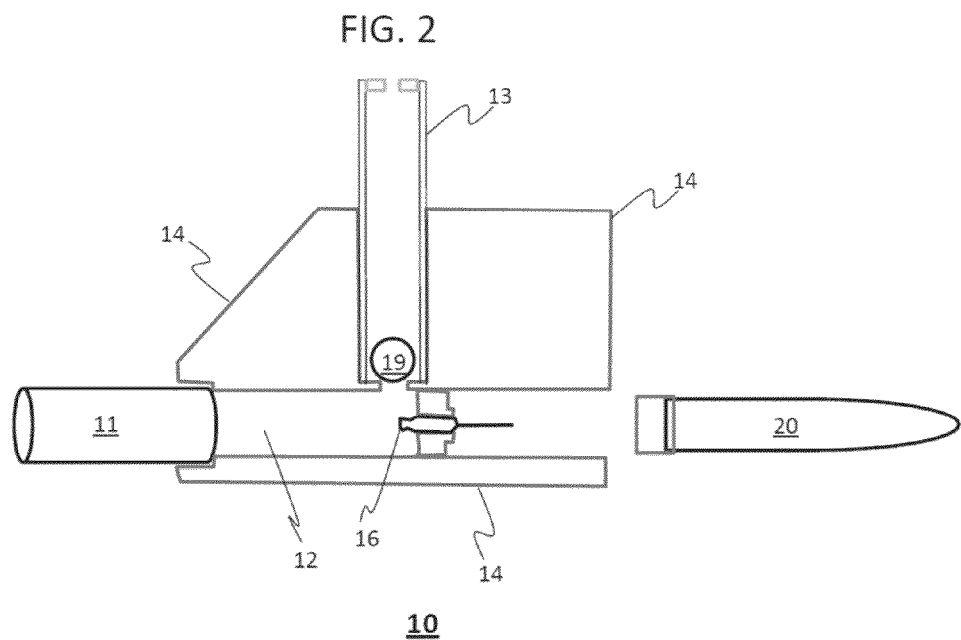

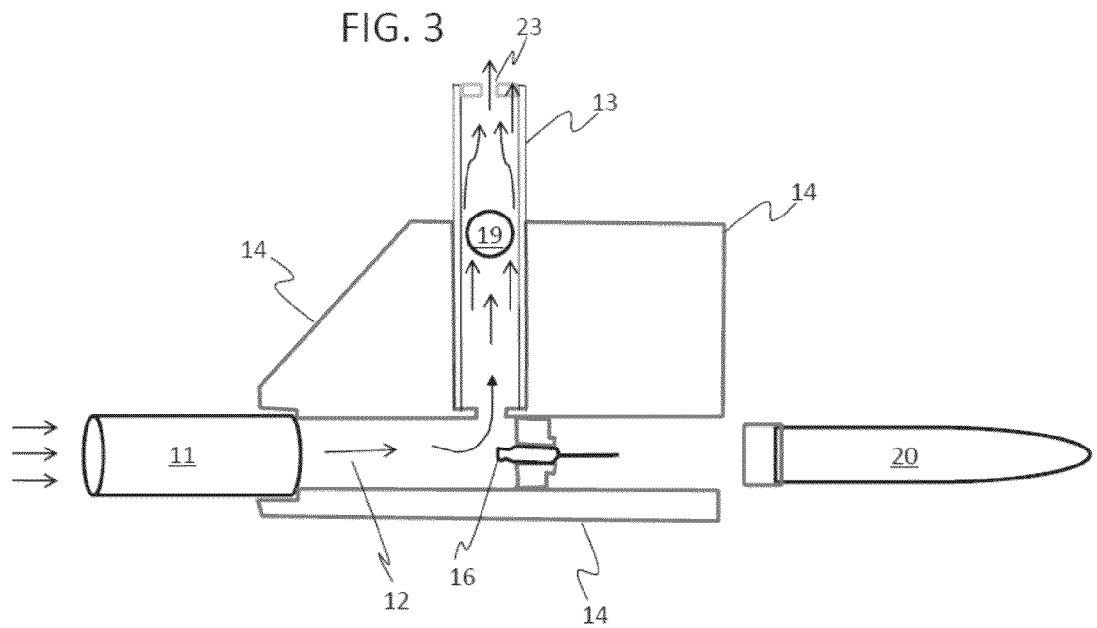
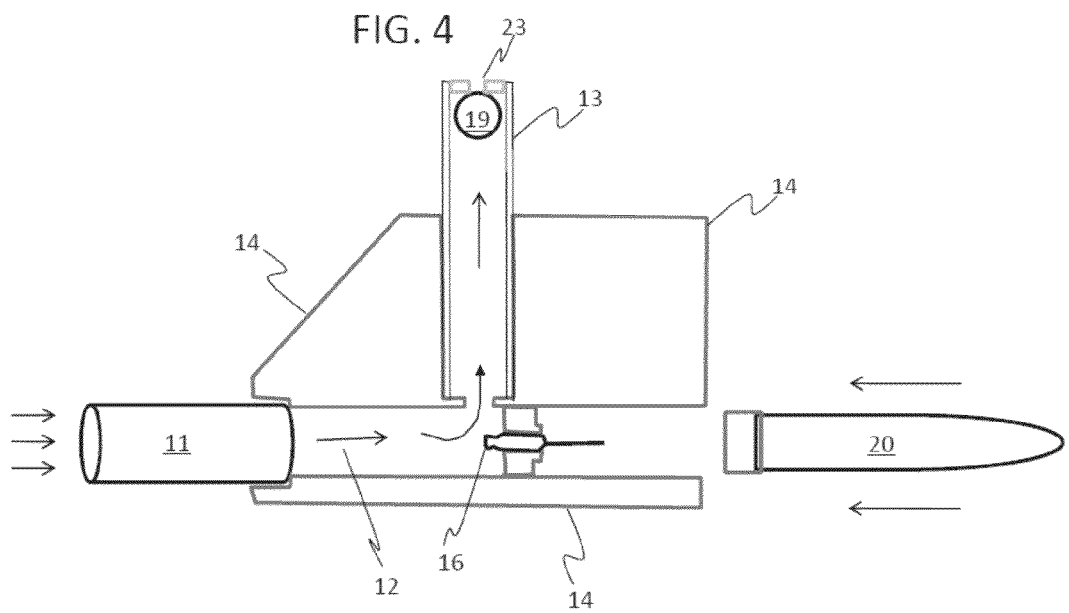

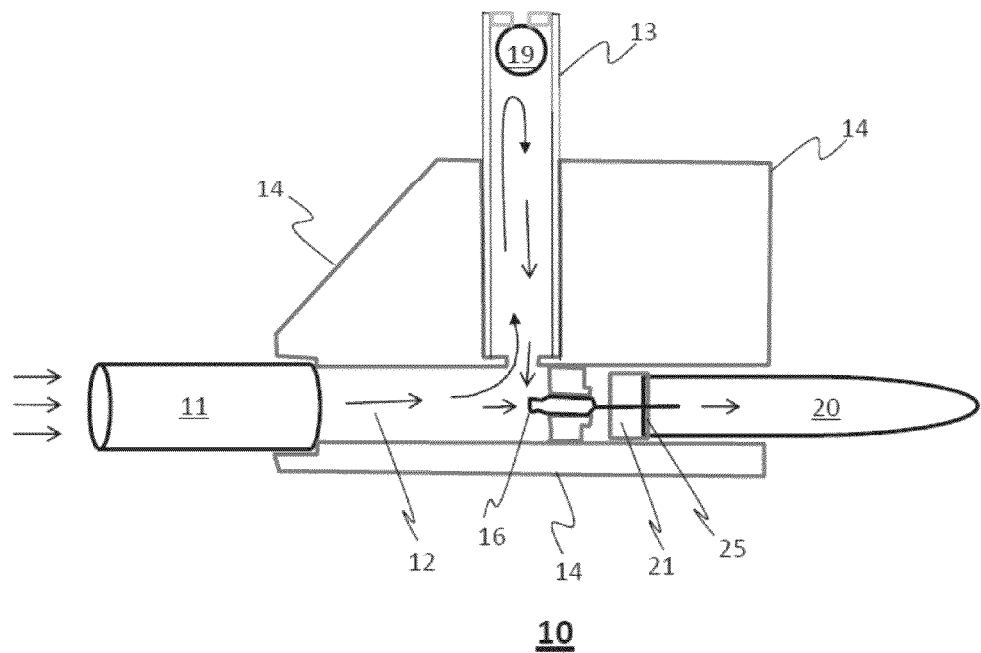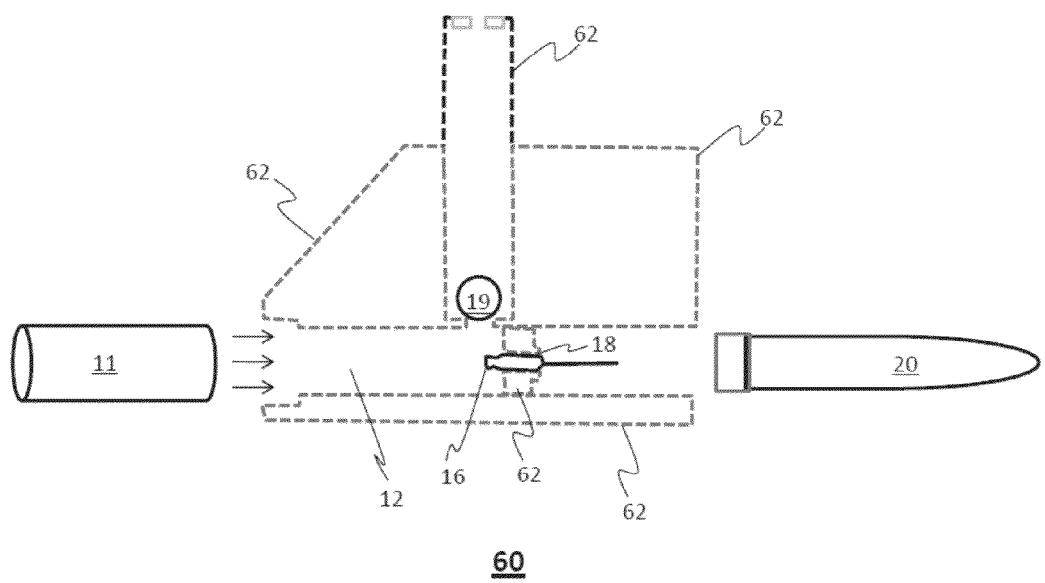

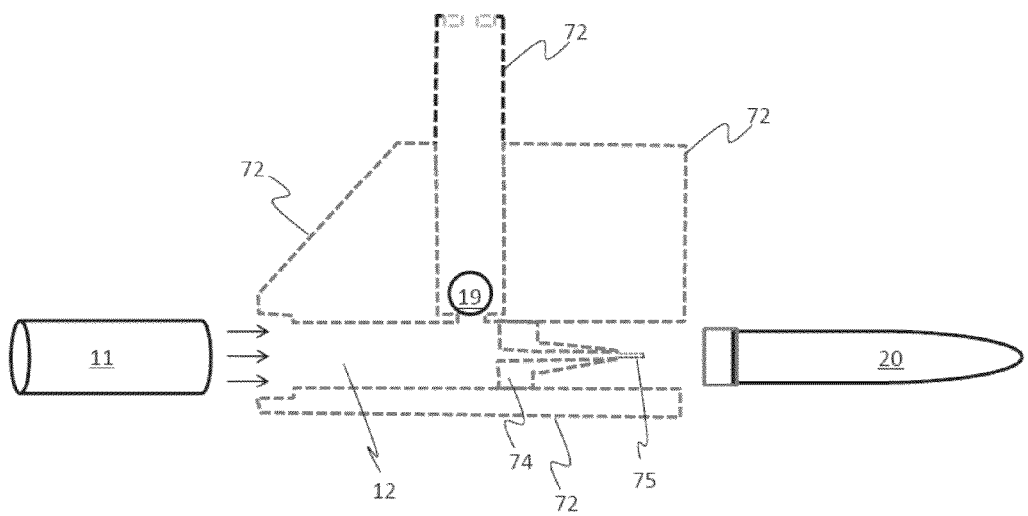
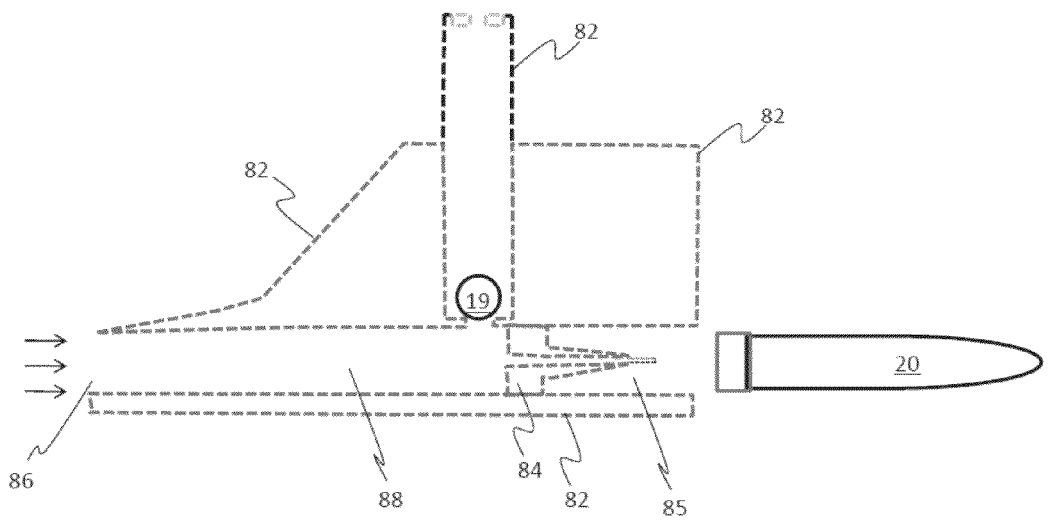

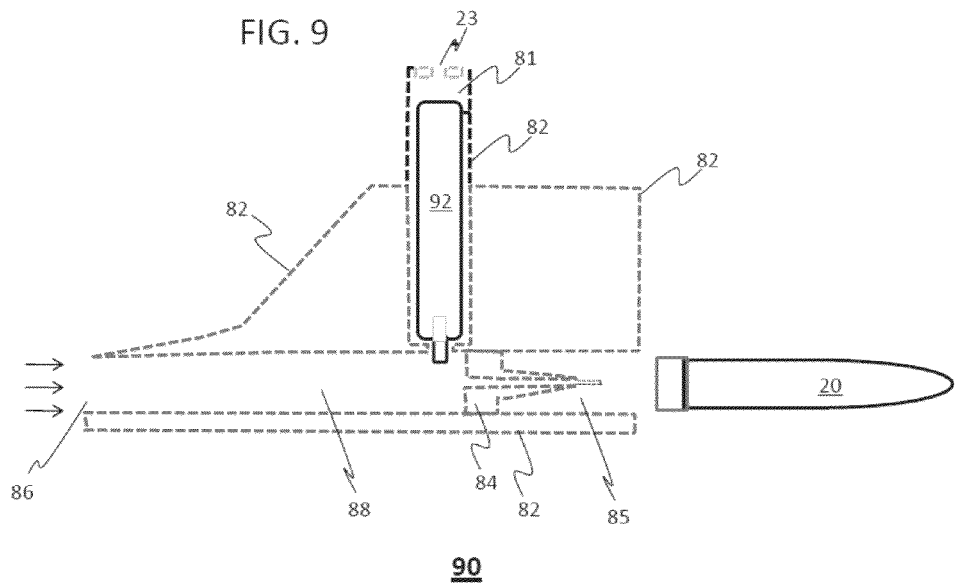
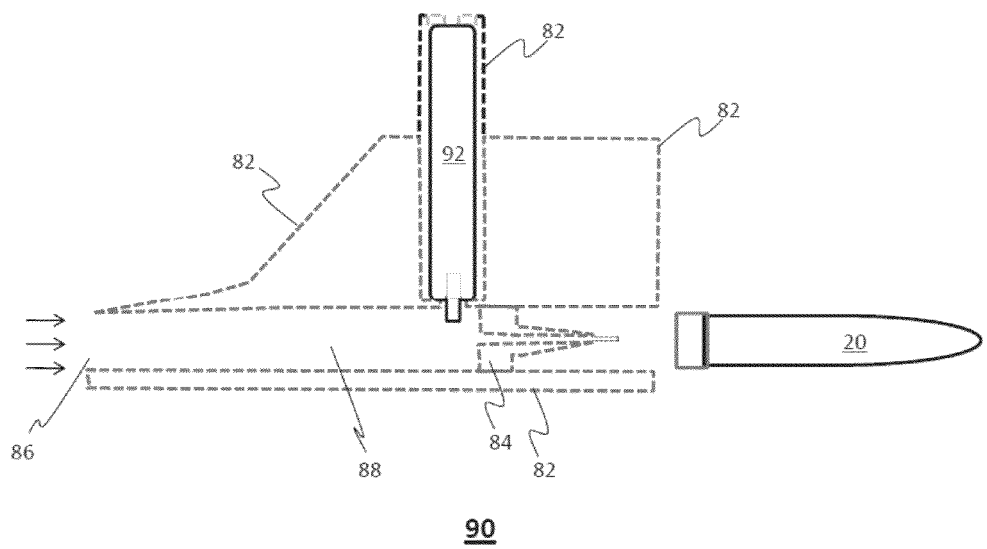

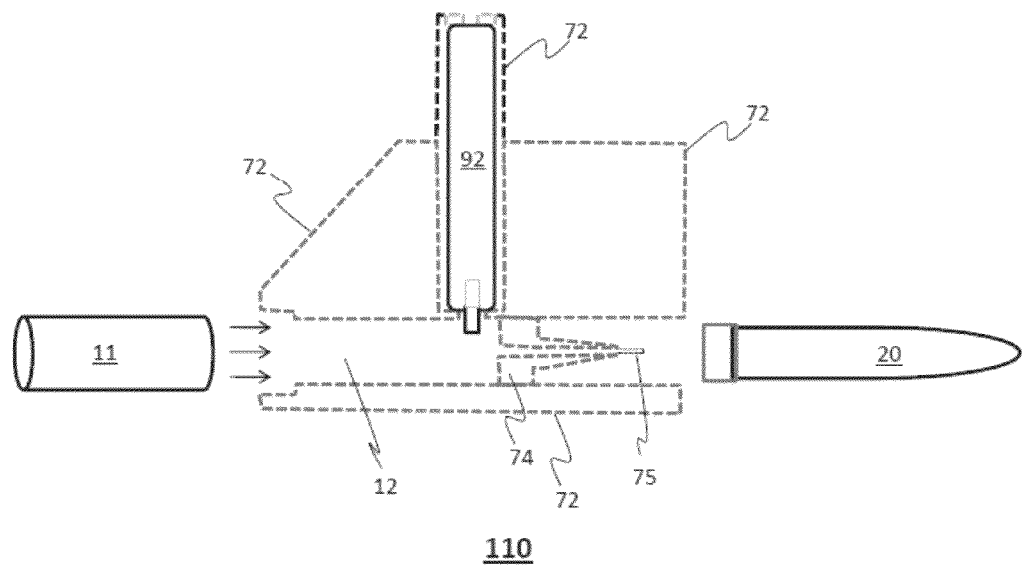
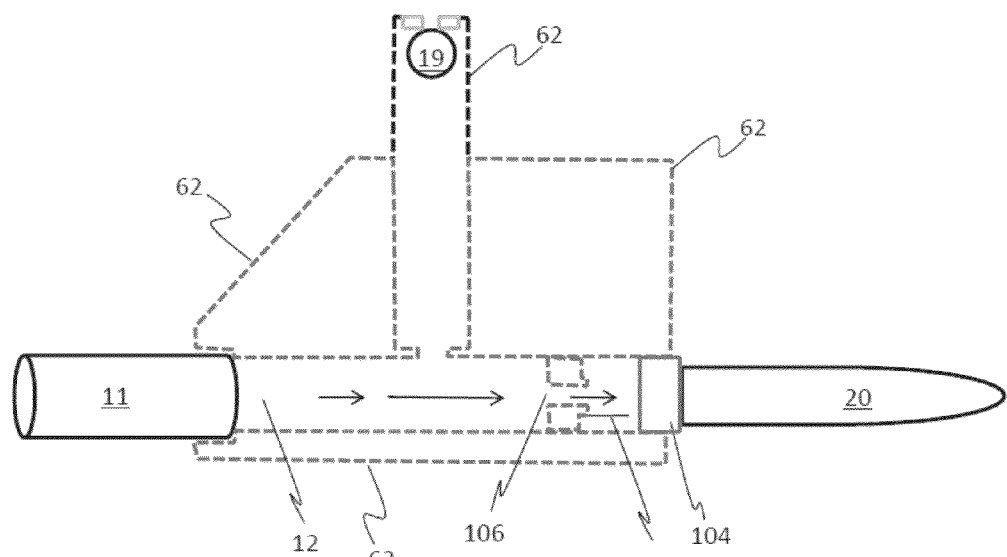

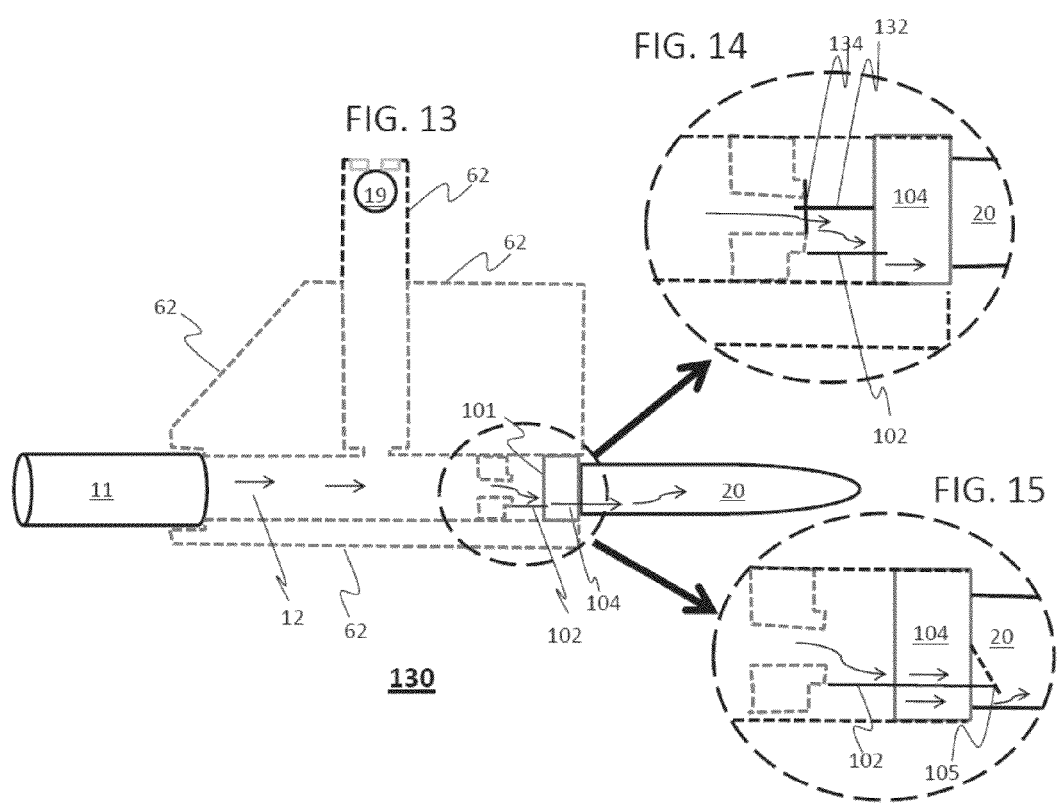

9,055,889 B2

METHOD AND APPARATUS FOR BREATH TESTING

FIELD OF THE DISCLOSURE

The present disclosure relates generally to the field of testing for various gases in breath and more specifically to a method and apparatus for the collection of exhaled breath samples for analysis.

BACKGROUND

Air from the lungs of a person can be used for a number of tests that would otherwise require the person to undergo an invasive type of testing or probing. For example, air from the alveoli of a person's lungs can be analyzed for the noninvasive diagnosis of *helicobacter pylori* (a stomach infection related to a high incidence of ulcers). Generally, a sufficient volume of air representative of true alveolar air is needed for accurate testing of bacteria or other components of a sample.

U.S. Pat. No. 5,467,776 by Steven D. Hamilton, uses a simple blow tube having a sampling port to capture sample air via an evacuated test tube. The blow tube can be connected to a waste air collection bag. A threaded needle assembly having a needle and placed in the sampling port of the blow tube is used to capture a breath sample by inserting the evacuated test tube into a capture assembly connected to the blow tube. Blowing into the blow tube directs a large portion of a patient's breath into waste collection bag and a remaining portion is directed through the needle assembly and needle connected to the sampling port of the blow tube. The technique described in the '776 patent has the variable of potentially drawing in an inconsistent ratio of waste air with the desired sample alveolar air.

BRIEF DESCRIPTION OF THE DRAWINGS

FIG. 1 is an exploded side view of a breath test apparatus in accordance with the embodiments before the insertion of a blow tube;

FIG. 2 is the breath test apparatus of FIG. 1 after insertion of the blow tube;

FIG. 3 is the breath test apparatus of FIG. 2 after blowing into the blow tube;

FIG. 4 is the breath test apparatus of FIG. 3 after blowing into the blow tube sufficiently to seal an exhaust port of a second output chamber of the breath test apparatus but before insertion of an evacuated tube and capture of a breath sample;

FIG. 5 is the breath test apparatus of FIG. 4 after blowing into the blow tube sufficiently to seal an exhaust port of a second output chamber using a float element and further insertion of the evacuated tube for capture of the breath sample;

FIG. 6 is an exploded side view of a similar breath test apparatus as the shown in FIG. 1, but having an integrated main housing including an integrated second output chamber;

FIG. 7 is an exploded side view of a similar breath test apparatus as the breath test apparatus of FIG. 6, but further having an integrated needle assembly integrated as part of the integrated main housing;

FIG. 8 is an exploded side view of a breath test apparatus having an extended input chamber integrated as part of the integrated main housing;

FIG. 9 is an exploded side view of a breath test apparatus similar to the breath test apparatus of FIG. 8, but using a self sealing apparatus in the form of a bladder within a second output or exhaust chamber instead of the floating element;

FIG. 10 is an exploded side view of the breath test apparatus of FIG. 9 showing the bladder fully inflated;

FIG. 11 is an exploded side view of the breath test apparatus of FIG. 7, but using a bladder instead of the floating element as part of a self sealing apparatus;

FIG. 12 is a side view of an alternative breath test apparatus having a puncture needle in a first output chamber;

FIG. 13 is a side view of FIG. 1 having the puncture needle piercing a membrane covering the opening of an evacuated tube;

FIG. 14 is an exploded view of a portion of FIG. 13 and further including au alternative embodiment having a membrane covered port between an input chamber and a first output chamber of the breath test apparatus; and FIG. 15 is an exploded view of a portion of FIG. 13 and further including an alternative embodiment having a stopper with a flapper member that provides a re-sealable test tube.

DETAILED DESCRIPTION

The present disclosure describes, among other things, illustrative embodiments of the breath testing apparatus. Other embodiments are contemplated by the present disclosure.

One embodiment of the present disclosure includes a breath sampling device comprising a main housing having a plurality of chambers, a blow tube for insertion within an input chamber of the main housing where the input chamber comprises a first port and a second port, a first output chamber of the main housing for capturing sample air through the first port, and a second output chamber in the main housing coupled to the input chamber through the second port of the input chamber where the second output chamber comprises an exhaust port. The breath sampling device can further comprise a float element within the second output chamber configured to freely move within the second output chamber and block the exhaust port when a predetermined amount of initial waste air fills the second output chamber.

A second embodiment of the present disclosure includes a breath sampling device, comprising a main housing having an input chamber, a first output chamber, and a second output chamber integrally formed therein where the input chamber and the first output chamber are coupled via a first port and the input chamber and the second output chamber are coupled via a second port, and a self-scaling apparatus within the second output chamber configured to seal at least an exhaust port of the second output chamber when a predetermined amount of initial waste air fills the second output chamber. The main housing can be configured to redirect a portion of air blown there through towards the output chamber via the first port when the self-sealing apparatus at least seals the exhaust port.

A third embodiment of the present disclosure includes a method of sampling expelled gas using a sampling device, the sampling device comprising a main housing having an input chamber, a first output chamber, and a second output chamber integrally formed therein where the input chamber and the first output chamber are coupled via a first port and the input chamber and the second output chamber are coupled via a second port, a self-scaling apparatus within the second output chamber configured to seal at least an exhaust port of the second output chamber when a predetermined amount of initial air fills the second output chamber. The method comprises receiving a sample of air including an initial volume of air from a patient through the input chamber, sealing the exhaust port by using at least the initial volume of air to force the self-sealing apparatus to at least block the exhaust port, and redirecting air through the first port toward the output chamber after sealing the exhaust port where a predetermined volume of air is captured within a vacuum of an evacuated tube having a sealed end that is temporarily provided access to a portion of the sample of air through the first port when the sealed end is pierced causing the vacuum to be replaced with the portion of the sample air.

FIG. 1 depicts an illustrative embodiment of a breath sampling device 10 comprising a main housing 14 having a plurality of chambers including an input chamber 12; a first output chamber 15, and a second output chamber 13. The device 10 can further include a blow tube 11 for insertion within the input chamber 12 of the main housing 14. The input chamber 12 can include a first port 18 and a second port 22. The second port 22 will generally have a larger aperture than the first port 18 (or 17) in order to direct initially blown air within the second output chamber 13 before redirecting air towards the first output chamber.

The first output chamber 15 of the main housing 11 can be used for capturing sample air through the first port 18. The second output chamber 13 in the main housing can be coupled to the input chamber 12 through the second port 22 of the input chamber where the second output chamber 13 comprises an exhaust port 23. Within the second output chamber 13 is a self sealing apparatus such as a float element 19 configured to freely move within the second output chamber 13 and block the exhaust port 23 when a predetermined amount of initial waste air fills the second output chamber 23. Note that the air within a patient's mouth, nose, and trachea can be considered "waste air" since it is not alveolar air from the lungs. When blowing into the breath sampling device 10, a portion of the initial air blown by the patient into the device will be waste air and a subsequent portion from the same breath will be desirable air or primarily alveolar air from a patient's lung or lungs.

FIGS. 1-5 illustrate the sequential steps in one particular embodiment using breath sampling device 10. FIG. 1 is before initial assembly where a blow tube 11 is about to be inserted into the input chamber 12 of the main housing 14 and FIG. illustrates the blow tube 11 inserted within the input chamber 12. Operationally, the initial air blown by the patient will force the floating element 19 to rise within the second output chamber 23 as illustrated in FIG. 3 until the floating element 19 reaches and blocks the exhaust port 23 as shown in FIG. 4. Before blocking the exhaust port 23, a portion of the waste air will traverse the side of the floating element and escape out of the exhaust port 23 as shown in FIG. 3 and otherwise generally remain in the second output chamber. Once the exhaust port 23 is blocked, blown air will be redirected towards and through the first port 18 to the first output port 15 and into an evacuated test tube 20 as illustrated in FIG. 5. The first port 18 can be constricted using a needle assembly 16 affixed within an aperture of the first port 18. The needle assembly can include a thin tube or needle 17 that is used to pierce re-sealable membrane 25 covering an opening of an evacuated test tube 20 having a vacuum. The re-sealable membrane 25 can be made of any re-sealable material such as rubber or silicone. The evacuated tube 20 can also include a stopper 21 such as a rubber stopper. The evacuated test tube 20 can be placed within the first output chamber 15 and where the main housing 14 and evacuated test tube 20 is configured to receive a portion of the air blown through the blow tube 11 and input chamber 12 when the re-sealable membrane 25 is punctured by a feed-through member such as the needle assembly 16 and needle 17 that can reside between the input chamber 12 and the first output chamber 15. The feed-through member can be integrally formed within (as shown in FIGS. 1-5) or form a part of an integrated main housing as shown in the breath testing devices 60 or 70 of FIG. 6 or 7 respectively. The feed-through member can generally be affixed to an aperture in an internal wall of the main housing between the input chamber 12 and the first output chamber 15. Note that the needle assembly 74 and the needle 75 can be integrally formed as part of the main housing 72 as illustrated in FIG. 7. In FIG. 6, the first port 18 is integrally formed as part of the main housing 62 and the needle assembly 16 is separately affixed to the first port 18 as in FIGS. 1-5. The needle assembly can be affixed in any number of ways to the first port 18 such as being glued or press fit into the first port 18.

Referring to FIGS. 1-5, the second output chamber 13 can comprise a tube having opposing constricted ends. One of the constricted ends can form the exhaust port 23 and a second of the constricted ends forms at least a portion of the second port 22 of the input chamber 12. In other alternative embodiments as illustrated in FIGS. 6-13, the second output chamber and the exhaust port 23 are integrally formed from the main housing. For example, the second output chamber is part of the main housing 62 in FIGS. 6, 12 and 13, and part of the main housing 72 or 82 in FIGS. 7 and 9-11. In one embodiment, the main housing can be a unitary housing or a housing formed primarily or entirely from two halves made of rigid plastic for example. In one embodiment, the second output chamber 13, 62, or 72 can be formed of a clear or substantially translucent material enabling visual confirmation when the floating element or other sealing element blocks the exhaust port 23.

Referring to FIG. 8, another embodiment of a breath testing device 80 similar to the embodiment of FIG. 7 is illustrated except that the main housing 82 can be formed to completely eliminate the need for the blow tube 11 found in FIGS. 1-7 by forming an input chamber 88 having an opening 86. In all other respects, the breath testing device 80 can be configured similarly to the breath testing device 70 of FIG. 7 including an integrated needle assembly 84 similar to the needle assembly 74 of FIG. 7.

FIG. 9 depicts an illustrative embodiment of another alternative breath sampling device 90 comprising a main housing 72 having an input chamber 88 and opening 86 similar to the embodiment of FIG. 8, a first output chamber 85, and a second output chamber 81 integrally formed as part of the main housing 82 where the input chamber 88 and the first output chamber 85 are coupled via a first port and the input chamber 88 and the second output chamber 81 are coupled via a second port. A self-sealing apparatus 92 within the second output chamber 8 lean be configured to seal at least an exhaust port 23 of the second output chamber when a predetermined amount of initial waste air fills the second output chamber 81. In FIG. 9, the bladder 92 is only partially filled and therefore not blocking the exhaust port 23 yet. The main housing 82 can be configured to redirect a portion of air blown there through towards the output chamber 85 via the first port when the self-scaling apparatus 92 at least seals the exhaust port. In one embodiment, the self-sealing apparatus 92 formed of a bladder can further seal off the second port as well when the bladder is filled or substantially filled with primarily waste air. Note that the self-sealing apparatus can alternatively comprise the float element 19 previously shown in other embodiments within the second output chamber configured to freely move within the second output chamber and block the exhaust port when a predetermined amount of initial waste air fills the second output chamber. In the embodiments of FIGS. 9-11, the self-sealing apparatus 92 comprises a bladder within the second output chamber 81 configured to fill the bladder with the predetermined amount of initial waste air to expand the bladder and causing the bladder to block the exhaust port once filled or substantially filled. The bladder can be further configured to block both the exhaust port and the second port once filled or substantially filled as illustrated in FIGS. 10 and 11.

The breath testing device 110 of the embodiment of FIG. 11 is similar to the embodiment of FIG. 7, except the self-sealing apparatus or bladder 92 replaces the floating element 19. As in other embodiments, the embodiments of FIGS. 6-14 can comprise an evacuated test tube 20 containing a vacuum and having a re-sealable membrane, and a second output chamber formed of clear or substantially translucent material enabling visual confirmation when the self sealing apparatus seals the exhaust port. Although the clear or substantially clear material is not necessarily, the visual cues it provides assist in providing consistent sampling. As in other embodiments, the evacuated test tube 20 can be placed within the first output chamber where the main housing and evacuated test tube is configured to receive a portion of the air blown through the input chamber when the re-sealable membrane is punctured by a feed-through member that resides between the input chamber and the first output chamber. The feed-through member can be a needle assembly affixed within an aperture in an internal wall of the main housing between the input chamber and the first output chamber.

Referring to FIG. 12, yet another alternative embodiment is illustrated showing a breath testing apparatus 120 similar to the embodiment of FIG. 6. However, the first port 106 between the input chamber 12 and an output chamber is configured differently and without the use of a needle assembly that passes air through the needle. Instead the blown air just passes through the first port 106 and the first output chamber. The evacuated test tube 20 can have a specifically designed stopper 104 that press fits into the first output chamber. When air is blown through the first port 106 and the evacuated test tube 20 and stopper 104 is press fit within the first output chamber, a portion of the blow air remains trapped within the output chamber until the evacuated test tube and stopper 104 is pushed into far enough into the first output chamber to cause a needle 102 to puncture a re-sealable membrane 101 on evacuated test tube 20 as illustrated in the breath testing device 130 of FIG. 13. Once the membrane 101 is ruptured or punctured by the needle 102, the vacuum in the evacuated test tube 20 will draw in the desired sample air within the second output chamber as more air is primarily drawn in from the input chamber 12.

Referring to FIG. 14, yet another alternative embodiment can further include a second needle 132 that forms a part of the stopper 104 and is used to puncture a membrane or flap 134 that covers the first port. Referring to FIG. 15, is yet another alternative embodiment that includes a stopper having a flapper 105 that temporarily draws in sample air to replace the vacuum in the evacuated test tube 20 when the test tube and stopper 104 are pushed in far enough with the first output chamber to have a needle 102 go through the stopper and push the flapper 105 open. Once the test tube 20 (and stopper 104) is removed from the first output chamber, the flapper is biased to close and reseal the test tube now containing the desired sampled air.

Illustrative embodiments of a method of sampling expelled gas using a sampling device as illustrated in FIGS. 1-15 can be applied to portions of the devices shown therein. The method can be used with a sampling device comprising a main housing having an input chamber, a first output chamber, and a second output chamber integrally formed therein, wherein the input chamber and the first output chamber are coupled via a first port and the input chamber and the second output chamber are coupled via a second port, a self-sealing apparatus within the second output chamber configured to seal at least an exhaust port of the second output chamber when a predetermined amount of initial air fills the second output chamber. The method can comprise receiving a sample of air including an initial volume of air from a patient through the input chamber, sealing the exhaust port by using at least the initial volume of air to force the self-sealing apparatus to at least block the exhaust port, and redirecting air through the first port toward the output chamber after sealing the exhaust port. A predetermined volume of air is captured within a vacuum of an evacuated tube for example having a sealed end that is temporarily provided access to a portion of the sample of air through the first port when the sealed end is pierced causing the vacuum to be replaced with the portion of the sample air. The method can further comprise visually confirming that the exhaust port is blocked before piercing the sealed end of the evacuated tube.

Upon reviewing the aforementioned embodiments, it would be evident to an artisan with ordinary skill in the art that said embodiments can be modified, reduced, or enhanced without departing from the scope and spirit of the claims described below. For example, as noted above, some of the functions performed by a self sealing apparatus can be performed using various alternative embodiments such as a floating element 19 or a bladder 92. The evacuated tube is not limited to an evacuated test tube having a stopper, but can have any type of re-sealable mechanism to capture the desired sample air. One embodiment uses a re-sealable membrane and yet another uses a stopper having a flapper that is temporarily opening with a needle or pin. The embodiments herein include are merely examples of the contemplated scope of the claims. Other embodiments are contemplated by the present disclosure.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A breath sampling device, comprising:
a main housing having a plurality of chambers;
a blow tube for insertion within an input chamber of the main housing, wherein the input chamber comprises a first port and a second port;
a first output chamber of the main housing for capturing sample air through the first port;
a second output chamber in the main housing coupled to the input chamber through the second port of the input chamber, wherein the second output chamber comprises an exhaust port;
a self-sealing apparatus comprising one of a bladder within the second output chamber configured to fill the bladder with a predetermined amount of initial waste air to expand the bladder and causing the bladder to block the exhaust port or a float element in the form of a ball or sphere within the second output chamber configured to freely move within the second output chamber and seal the exhaust port when the predetermined amount of initial waste air fills the second output chamber;
wherein the main housing is configured to redirect a portion of air blown therethrough towards the output chamber via the first port when the float element or the bladder within the second output chamber at least seals the exhaust port.

2. The breath sampling device of claim 1 further comprising an evacuated test tube containing a vacuum and having a re-sealable membrane.

3. The breath sampling device of claim 2, wherein the evacuated test tube is placed within the first output chamber and wherein the main housing and evacuated test tube is configured to receive a portion of the air blown through the blow tube and input chamber when the re-sealable membrane is punctured by feed-through member that resides between the input chamber and the first output chamber.

4. The breath sampling device of claim 3, wherein the feed-through member is integrally formed within the main housing.

5. The breath sampling device of claim 3, wherein the feed-through member is a needle assembly affixed to an aperture in an internal wall of the main housing between the input chamber and the first output chamber.

6. The breath sampling device of claim 1, wherein the second output chamber comprises a tube having opposing constricted ends, one of the constricted ends forming the exhaust port and a second of the constricted ends forming at least a portion of the second port of the input chamber.

7. The breath sampling device of claim 1, wherein the second output chamber and the exhaust port are integrally formed from the main housing.

8. The breath sampling device of claim 1, wherein the main housing is a unitary housing or a housing formed of two halves made of plastic.

9. The breath sampling device of claim 1, wherein the second output chamber is formed of a clear or substantially translucent material enabling visual confirmation when the floating element blocks the exhaust port.

10. A breath sampling device, comprising:
a main housing having an input chamber, a first output chamber, and a second output chamber integrally formed therein, wherein the input chamber and the first output chamber are coupled via a first port and the input chamber and the second output chamber are coupled via a second port;
a self-sealing apparatus within the second output chamber configured to seal at least an exhaust port of the second output chamber when a predetermined amount of initial waste air fills the second output chamber; and
wherein the main housing is configured to redirect a portion of air blown therethrough towards the output chamber via the first port when the self-sealing apparatus at least seals the exhaust port;
wherein the self-sealing apparatus comprises a bladder within the second output chamber configured to fill the bladder with the predetermined amount of initial waste air to expand the bladder and causing the bladder to block the exhaust port.

11. The breath sampling apparatus of claim 10, wherein the bladder when filled with the predetermined amount of initial waste air to expand the bladder causes the bladder to block the exhaust port and the second port.

12. The breath sampling device of claim 10 further comprising an evacuated test tube containing a vacuum and having a re-sealable membrane.

13. The breath sampling device of claim 10, wherein the second output chamber is formed of a clear or substantially translucent material enabling visual confirmation when the self-sealing apparatus seals the exhaust port.

14. The breath sampling device of claim 13, wherein the evacuated test tube is placed within the first output chamber and wherein the main housing and evacuated test tube is configured to receive a portion of the air blown through the input chamber when the re-sealable membrane is punctured by a feed-through member that resides between the input chamber and the first output chamber.

15. The breath sampling device of claim 14, wherein the feed-through member is a needle assembly affixed within an aperture in an internal wall of the main housing between the input chamber and the first output chamber.

16. The breath sampling device of claim 14 wherein the feed-through member is integrally formed within the main housing.

17. A method of sampling expelled gas using a sampling device, the sampling device comprising a main housing having an input chamber, a first output chamber, and a second output chamber integrally formed therein, wherein the input chamber and the first output chamber are coupled via a first port and the input chamber and the second output chamber are coupled via a second port, a self-sealing apparatus within the second output chamber configured to seal at least an exhaust port of the second output chamber when a predetermined amount of initial air fills the second output chamber, the method comprising:
receiving a sample of air including an initial volume of air from patient through the input chamber;
sealing the exhaust port by using at least the initial volume of air to force the self-sealing apparatus to at least block the exhaust port, wherein the self-sealing apparatus comprises one of a bladder within the seond output chamber configured to fill the bladder with the predetermined amount of initial volume of air to expand the bladder and causing the bladder to block the exhaust port or float element in the form of a ball or sphere within the second output chamber configured to freely move within the second output chamber and seal the exhaust port when the predetermined amount of initial volume of air fills the second output chamber, and after sealing the exhaust port, redirecting air through the first port toward the output chamber, wherein a predetermined volume of air is captured within a vacuum of an evacuated tube having a sealed end that is temporarily provided access to a portion of the sample of air through the first port when the sealed end is pierced causing the vacuum to be replaced with the portion of the sample air.

18. The method of claim 17, comprising visually confirming that the exhaust port is blocked before piercing the sealed end of the evacuated tube.

* * * * *